United States Patent
Berndtsson et al.

(10) Patent No.: US 7,608,223 B2
(45) Date of Patent: Oct. 27, 2009

(54) BLOOD TESTING APPARATUS

(75) Inventors: Ingemar Berndtsson, Sollentuna (SE); Lars Svensson, Vallentuna (SE); Lennart Niklason, Sollentuna (SE)

(73) Assignee: Boule Medical AB, Stockholm (SE)

( * ) Notice: Subject to any disclaimer, the term of this patent is extended or adjusted under 35 U.S.C. 154(b) by 729 days.

(21) Appl. No.: 10/533,790

(22) PCT Filed: Nov. 19, 2003

(86) PCT No.: PCT/SE03/01796

§ 371 (c)(1),
(2), (4) Date: May 4, 2005

(87) PCT Pub. No.: WO2004/045770

PCT Pub. Date: Jun. 3, 2004

(65) Prior Publication Data

US 2006/0013740 A1    Jan. 19, 2006

(30) Foreign Application Priority Data

Nov. 20, 2002   (SE) .................................. 0203435

(51) Int. Cl.
*B01L 3/00* (2006.01)
(52) U.S. Cl. ....................................................... 422/102
(58) Field of Classification Search .................. 422/102
See application file for complete search history.

(56) References Cited

U.S. PATENT DOCUMENTS 4,690,801 A    9/1987   Anderson et al.
5,230,866 A    7/1993   Shartle et al.
5,652,149 A    7/1997   Mileaf et al.
5,665,315 A    9/1997   Robert et al.
5,863,502 A *  1/1999   Southgate et al. ............. 422/58
6,284,548 B1   9/2001   Berndtsson
6,387,328 B1   5/2002   Berndtsson

FOREIGN PATENT DOCUMENTS

| EP | 0306158 A2 | 3/1989 |
|---|---|---|
| EP | 1 203 959 A1 | 5/2002 |
| WO | WO 93/17328 | 9/1993 |
| WO | WO-99/01742 A1 | 1/1999 |
| WO | WO-01/75416 A1 | 10/2001 |
| WO | WO-02/18785 A1 | 3/2002 |
| WO | WO-03/044488 A1 | 5/2003 |

* cited by examiner

*Primary Examiner*—Walter D Griffin
*Assistant Examiner*—Bobby Ramdhanie
(74) *Attorney, Agent, or Firm*—Birch, Stewart, Kolasch & Birch, LLP

(57) ABSTRACT

A disposable apparatus for use in blood testing includes a housing (21) having integrated means (41) for receiving a blood sample, a plurality of receptacles (28-33) for diluent and diluted sample, and a plurality of channels (34-39). Depressions are formed in a surface (27) of the housing to form the receptacles (28-33) and the channels. A diaphragm (40) seals the receptacles and the channels relative to said surface (27). When a pressure variation is applied to a portion of the diaphragm sealing a receptacle, liquid is caused to be displaced to or from that receptacle.

21 Claims, 7 Drawing Sheets

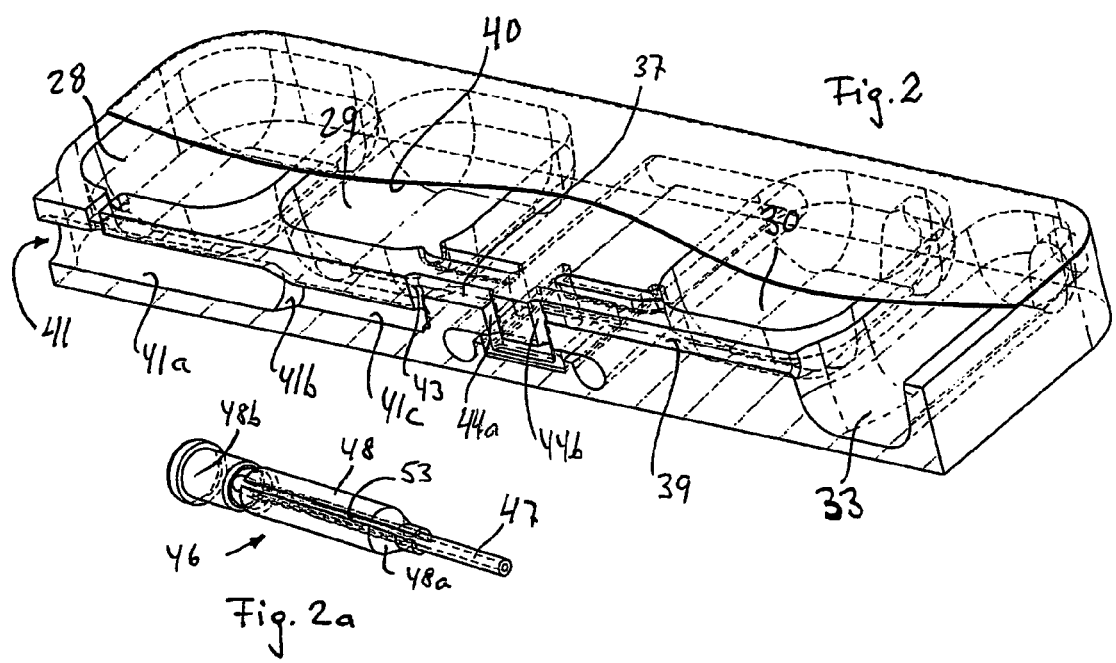

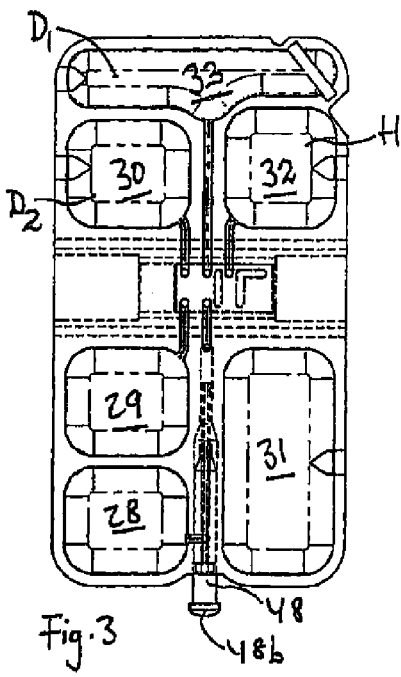
Fig. 3 Transport position
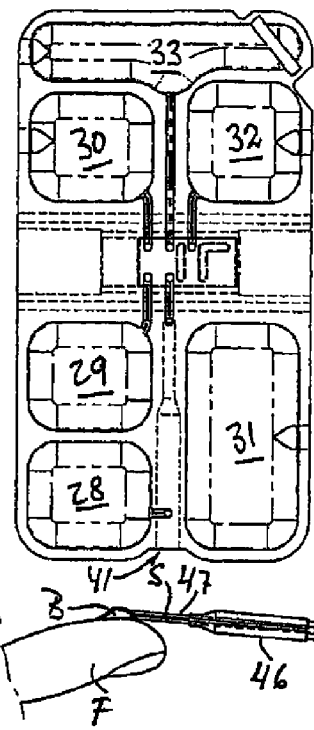
Fig. 4 Sampling
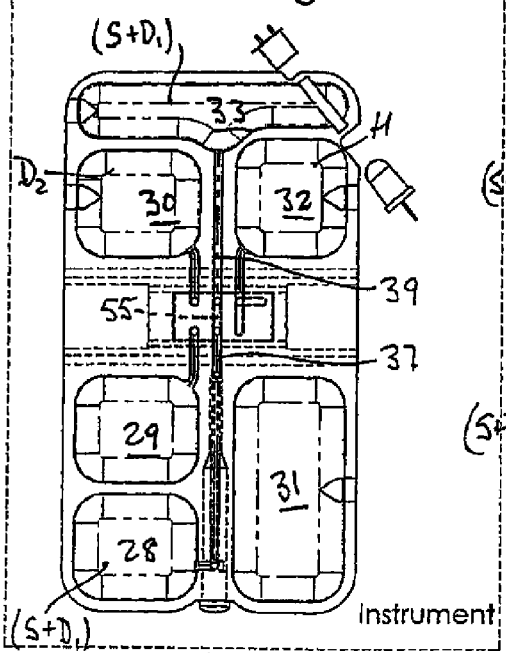
Fig. 5 First mixing
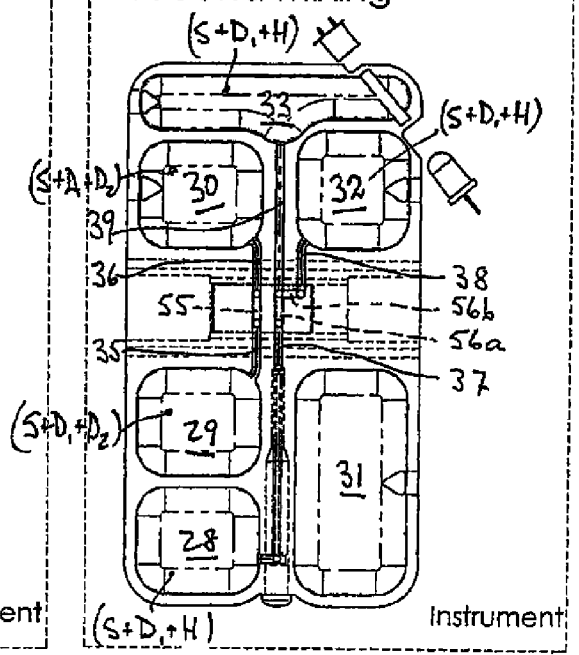
Fig. 6 Second mixing

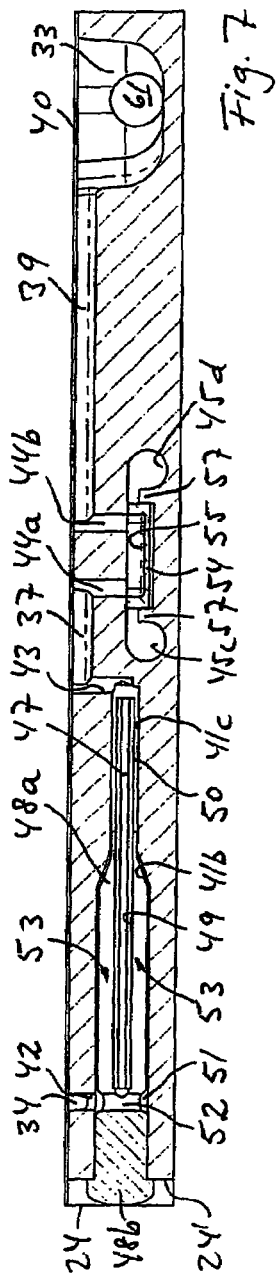
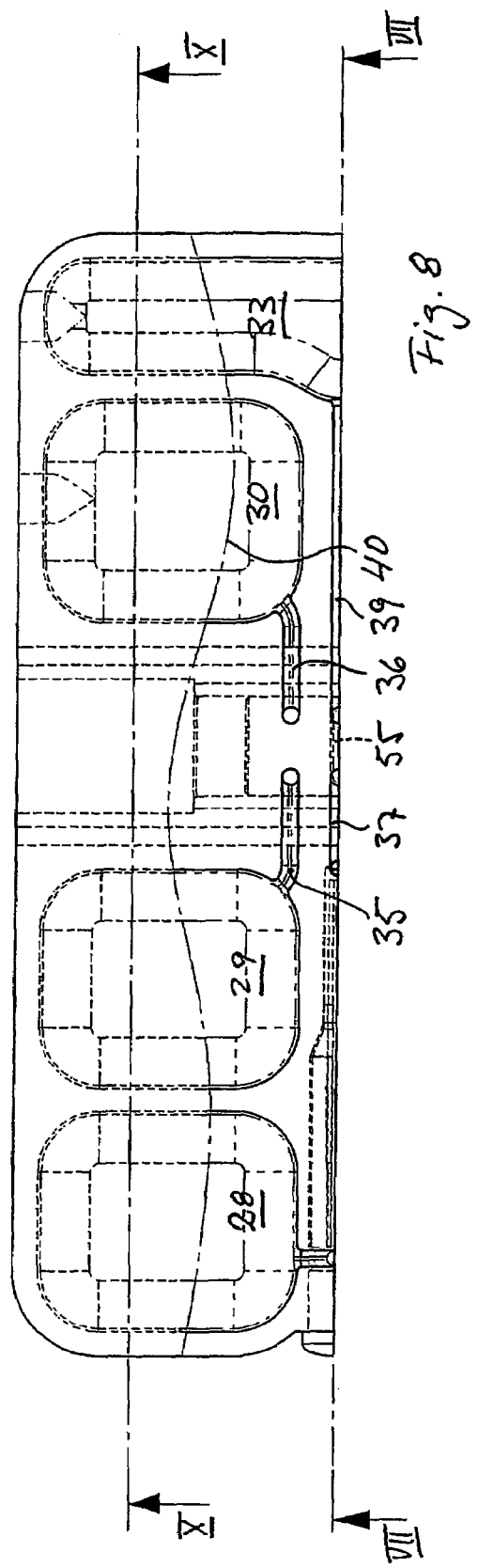

BLOOD TESTING APPARATUS

The present invention concerns a blood testing apparatus, an instrument for its operation and a method for operating the apparatus.

When making blood tests in the field, it is a desire to perform such tests with simple but reliable apparatus that can be handled even by relatively untrained personnel. Still, there exists the requirement that a blood sample shall be taken and handled under strict hygienic conditions, and that neither the sample itself or residues thereof, nor diluting or flushing liquids used when testing the sample shall risk to be contacted by humans. Thus, there shall be no waste matter and all contaminated material shall remain within the apparatus.

It is known in the state of art to count blood cells by causing a volume of diluted blood sample to pass a so-called capillary, i.e., an extremely small hole, generally in a ruby, the hole having a diameter considerably larger than the size of a blood cell, typically 80 µm. A voltage is applied over the capillary, and, when a blood cell passes through the hole, the electrical resistance changes. This is because the cells can be regarded as insulators. Each change in resistance can be detected by suitable electronic equipment, and the sum of all changes detected corresponds to the number of blood cells having passed through the capillary. In order to obtain the concentration of cells in the original sample, the concentration of cells in the diluted sample is multiplied by the dilution factor, typically 1:40000 when counting of red blood cells (RBC) is concerned. It is obvious, that measuring of sample volumes and dilution liquid volumes must be performed in an accurate and repeatable way such that not only a correct degree of dilution can always be guaranteed but also a thorough and uniform mixing of the two volumes is ensured.

A disposable sampling device for an apparatus for counting particles contained in a liquid, such as blood cells in a blood sample, is known from WO 99/01742. This device is capable of making one diluting step.

A blood testing apparatus for performing dilution of a small defined volume of blood sample contained in a capillary tube is described in U.S. Pat. No. 6,284,548. The dilution involves a pre-dilution step and a final dilution step.

A device for diluting and mixing a liquid sample, such as a blood sample for performing a CRP test, is described in WO 01/75416. The sample is contained in a capillary tube and is mixed in a first step with a diluting agent to provide a diluted sample. In a second step, a third medium, such as antibodies, may be mixed with the diluted sample.

Even if some of the prior art devices are capable of making two dilutions, none of them is capable of making two simultaneous dilutions to different dilution ratios, which is desirable in order to perform, e.g., simultaneous counting of white and red blood cells.

A disposable apparatus for use in blood testing, having one of the present co-inventors as single inventor, is described in SE 0103877-7 filed 21 Nov. 2001 and unpublished at the date of filing the present application. It presents one solution to the problem of providing such apparatus allowing simultaneous dilution of a blood sample to two defined dilutions ratios. It is also capable of retaining all contaminated material within itself.

This prior apparatus comprises a block-shaped housing having a first and a second receptacle; a first and a second cylinder, each having a piston moveable therein and each containing a defined volume of a diluent; a valve including a valve body having three valve body channels extending therethrough and being positionable in three distinct positions. In one position the receptacles are put in simultaneous communication with one each of the cylinders through pairs of the channels. One of the receptacles, as a first means for receiving a blood sample, is adapted to receive a blood sampling capillary tube.

Although fulfilling the objectives stated, this apparatus presents some inconveniences. One relates to the manufacture of the block-shaped housing, which is expensive and complicated due to its various cylinders, and makes it unsuited for injection moulding. Another relates to the use of cylinders as means for containing the diluent, and pistons movable within the cylinders to displace the diluent. It manifests itself particularly during air transportation when the pistons tend to move uncontrolled due to a varying surrounding air pressure.

The present invention has as its object to present an alternative solution to problem of providing a disposable apparatus for use in blood testing allowing simultaneous dilution of a blood sample to two defined dilutions ratios and being capable of retaining all contaminated material within itself.

To fulfill this object, the present invention proposes the disposable apparatus having the characterizing features, an instrument for controlling the apparatus and a method of controlling the apparatus, as defined in the appended claims.

According to the present invention there is provided a block-shaped housing or cartridge having depressions in at least one of its sides. The depressions form and define main portions of receptacles and channels in the housing open towards the side of the housing in which they are formed. A diaphragm is positioned over at least portions of that side to seal the respective receptacles and channels and to define one side thereof. Portions of the diaphragm positioned over receptacles are moveable relative to the plane of the side of the housing so as to cause a variation in the pressure within the receptacle, or, in response to a pressure variation, or, a volume variation therein. The channels interconnect the various receptacles and a valve provided within the housing to control flow between the receptacles.

An embodiment of the invention will now be described, reference being made to the accompanying drawings, wherein:

FIG. 2 is a perspective longitudinal central section through the cartridge of FIG. 1;

FIG. 2a is a perspective view of the capillary holder;

FIG. 3 is a plan view showing the cartridge in its transport position;

FIG. 4 is a plan view showing the cartridge in its sampling position and also showing the sampling device and a portion of a finger tip;

FIG. 5 is a plan view showing the cartridge in its first dilution or mixing position;

FIG. 6 is a plan view showing the cartridge in its second dilution or mixing position;

FIG. 7 is a longitudinal central section through the cartridge taken along line VII-VII in FIG. 8;

FIG. 8 is a plan view of one half of the cartridge showing portions of the diaphragm cut away;

Figure 1:
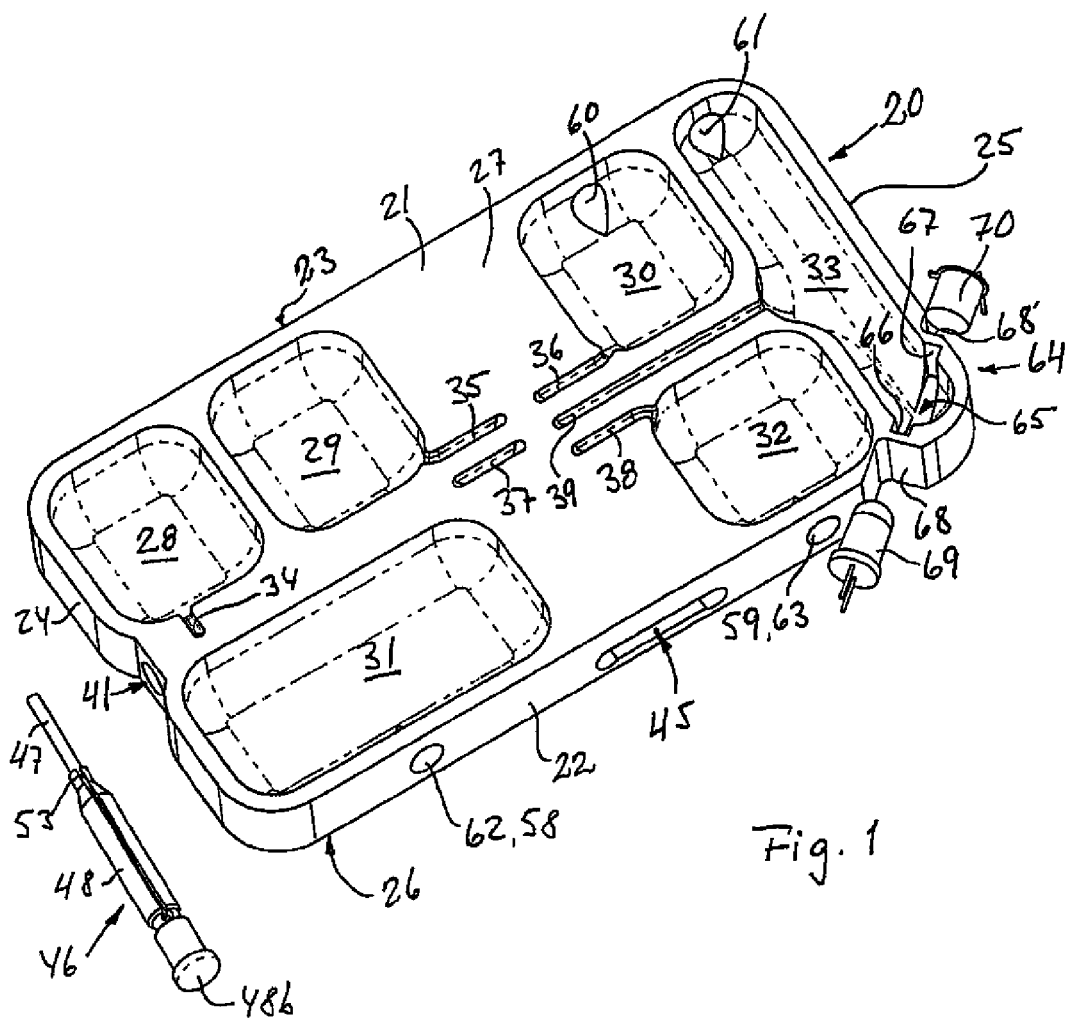
FIG. 1 is a perspective view of a cartridge having receptacles and channels in one of its sides, an associated sampling tube, and a photometer arrangement.

A cartridge 20 according to the present invention is shown in perspective in FIG. 1. It comprises a block-shaped, preferably molded housing 21 made from a preferably translucent material. It has a generally paralellepipedic shape including opposed longer side walls 22, 23, opposed shorter side walls 24, 25, a bottom side 26 and a top side 27. In the generally flat top side 27 is formed a plurality of depressions, in this embodiment six relatively large depressions defining receptacles 28-33, and five relatively narrow depressions defining channels 34-39.

A diaphragm 40 (FIGS. 2, 7, 8 and 10) is sealingly attached to the top side 27 of the housing 21 so as to cover all depressions forming the receptacles and channels and to seal them relative to the environment.

A hole 41 extends centrally from the shorter side wall 24 towards the middle of the housing (see particularly FIGS. 2 and 7). It includes an outer, relatively wide, cylindrical portion 41a merging by an intermediate, frustoconical portion 41b with an inner, relatively narrow cylindrical portion 41c.

Relatively close to its exterior end, a hole 42 connects the hole portion 41a to one end of the channel 34, whose opposite end opens in the receptacle 28.

At the inner end of the hole 41, a hole 43 connects its more narrow portion 41c to a first end of the channel 37, whose second, opposite end connects to a hole 44a opening into an aperture 45 extending crosswise through the housing 21 between its longer side walls 21 and 22.

The opening 41 serves for receiving a holder 46 for a capillary tube 47 in the housing 21. The capillary holder is particularly shown in FIGS. 1 and 2a, and is shown sectioned in its entirely introduced state in FIG. 7. It comprises a body 48 fitting into the wider portion 41a of the hole 41 and having a frustoconical portion 48a matching the frustoconical portion 41b of the hole 41. A cap portion 48b in the rear end of the body 48 abuts a recessed portion 24' of the side wall 24 around the mouth of the hole 41 so as to limit the extent of introduction of the capillary holder into the hole 41 (FIG. 7). A central hole 49 extending from the forward end of the capillary holder 46 receives a major portion of the capillary tube 47, the forward, free end of which opens close to where the hole 43 opens into the narrow portion 41c of the hole 41. The capillary tube 47 has a smaller outer diameter than the inner diameter of the hole portion 41c, thus leaving an annular space 50 between the capillary tube and the wall of the hole portion 41c. An annular groove 51 is formed in the body 48 to be located opposite to the hole 42, and a cross-hole 52 extends diametrically therethrough to open at opposed locations in the groove 51. The hole 52 intersects the hole 49 so as to establish communication between the annular groove 51 and the capillary tube 47 via the cross-hole 52, and, thereby, from the receptacle 28, through the channel 34, the hole 42, the groove 51, the cross-hole 52, the capillary tube 47, and the hole 43 to the channel 37.

As partly seen in FIG. 1 and more clearly in FIG. 7, the body 48 of the capillary holder 46 has a slot 53 extending from its foremost end to the annular groove 51, thus establishing communication between the annular space 50 and the annular groove 51. The slot 53 also makes the capillary holder flexible so as to facilitate introduction of the capillary tube 47 therein.

In the aperture 45 open one respective end of the channels 35, 36, 37, 38 and 39. The respective opposite end of these channels open in the receptacles 29, 30, 32 and 33.

Channels 35 and 36 are aligned, as are channels 37 and 39. Channels 35 and 37 are mutually parallel, as are channels 36, 38 and 39. The lateral spacing between channels 35 and 37 is equal to that between channels 36 and 39 as well as between channels 39 and 38.

Figure 9:
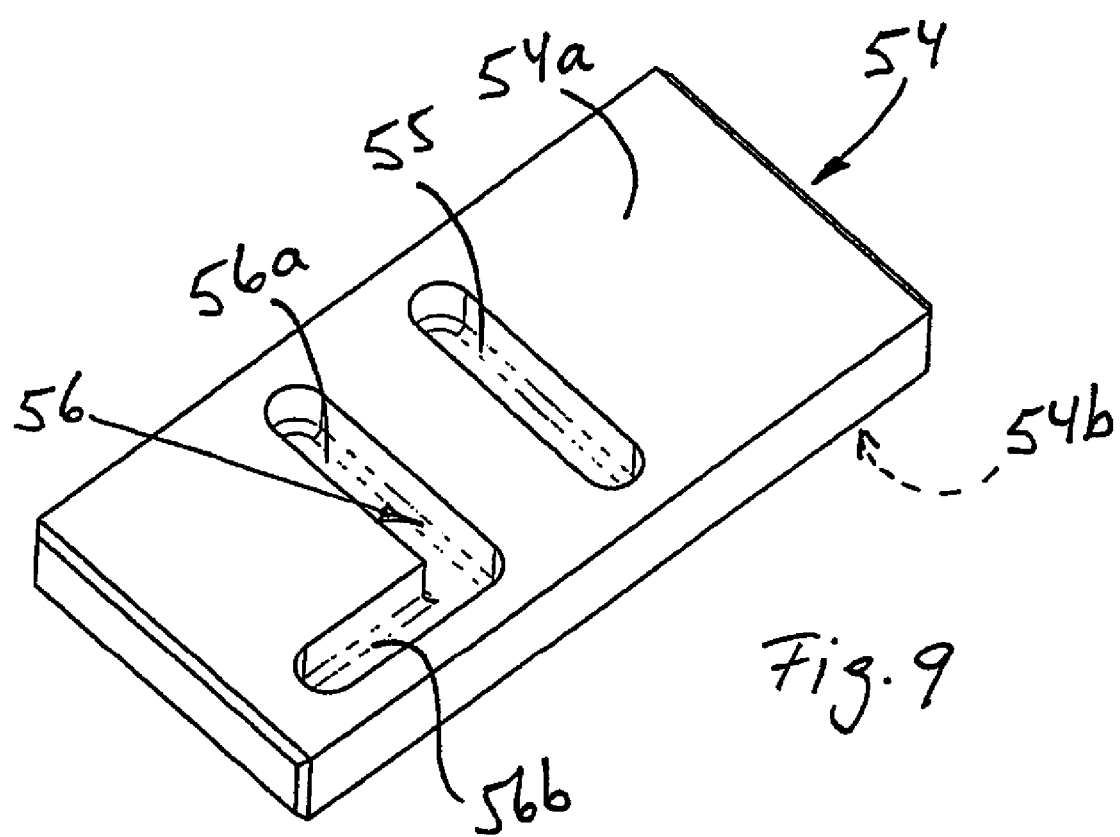
FIG. 9 is a perspective view of the valve slide.

The aperture 45 serves to slidingly receive a valve slide 54 shown in FIGS. 2 and 7, and separately shown in FIG. 9. It comprises a parallelepipedic body having opposed parallel surfaces 54a, 54b. In the surface 54a is formed a straight channel 55 extending in the crosswise direction of the aperture 45 and having a well-defined volume, typically 10 µl, and an L-shaped channel 56 having a first leg 56a extending in the crosswise direction of the aperture 45, i.e., parallel to the straight channel 55, and a second leg 56b extending perpendicularly thereto. The spacing between the channel 55 and the first leg 56a is equal to the lateral spacing between the channels 35/37 and 36/39/38, and the length of the second leg 56b is equal to the spacing between the channels 36 and 38.

Figure 10:
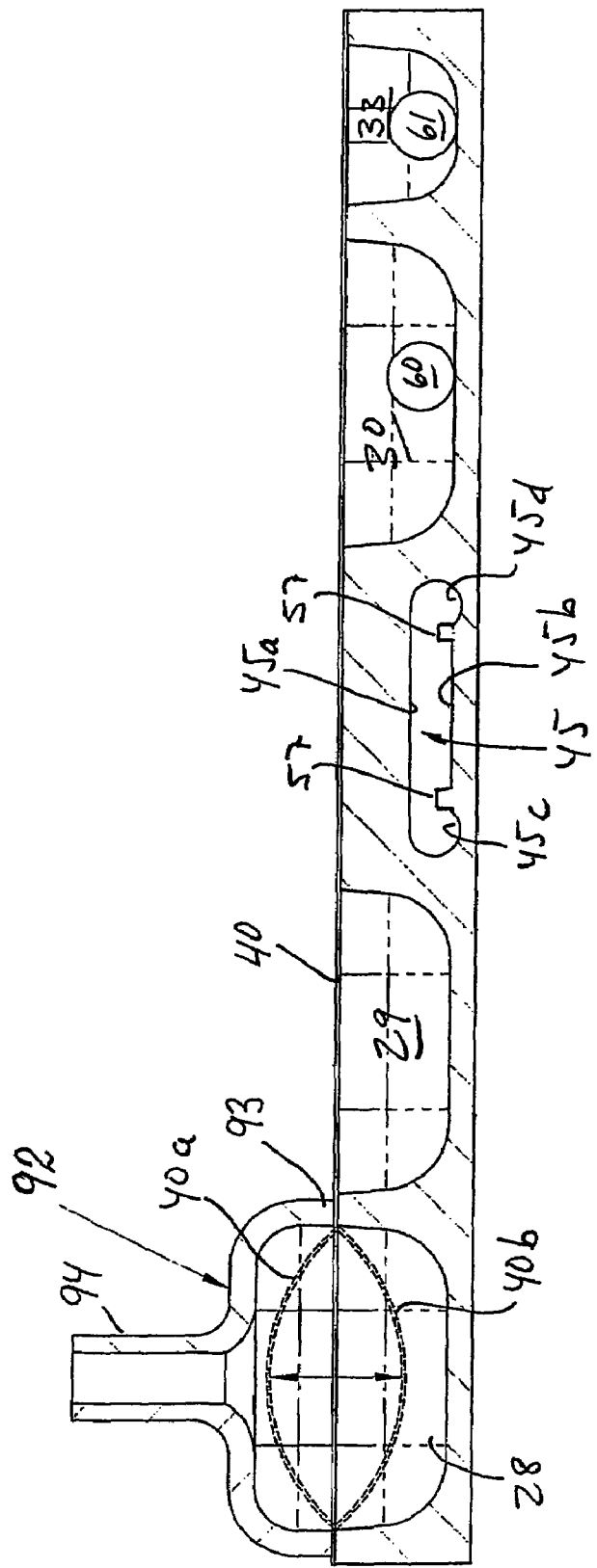
FIG. 10 is a section through the cartridge taken along line X-X in FIG. 8 showing more in detail the operation of the device.

The cross-sectional shape of the aperture 45 appears best from FIG. 10. It includes a central portion having parallel sides 45a, 45b for slidingly supporting the valve slide surfaces 54a, 54b, respectively. The valve slide 54 is laterally guided by parallel ribs 57 protruding from the surface 45b. In order not to make the material between the side 45b of the aperture and the bottom surface 26 of the body 21 flex due to introduction of the valve slide into the aperture 45, the aperture is widened beyond the ribs 57, and the material thickness is reduced along parallel, part-cylindrical recesses 45c, 45d, thereby imparting the remaining material spring properties urging the valve slide 54 towards the surface 45a of the aperture 45. Alternatively, the slide may be made with a certain degree of resilience to ensure proper sealing.

In the opposed longer side walls 22 and 23 of the housing are provided openings 58, 59, 60 and 61 providing access to the receptacles 31, 32, 30 and 33, respectively. After filling of these receptacles (see below), the openings are closed by plugs that are pierceable by an injection needle or the like in order to inject a fluid into or retract a fluid from the respective receptacles of the plugs, only plugs 62 and 63 sealing receptacles 31 and 32, respectively, are seen in FIG. 1.

The sequence of operation of the cartridge 20 will now be described with reference to FIGS. 3-6 showing four subsequent steps.

In FIG. 3 is shown the preparatory or transport position of the cartridge 20. In advance, a well-defined volume, typically 2 ml, of a liquid diluting agent $D_1$ has been filled into the receptacle 33 having a capacity of typically 3 ml. Likewise, a well-defined volume, typically 2 ml, of a liquid diluting agent $D_2$ has been filled into the receptacle 30 also having a capacity of typically 3 ml. The diluting agents are typically an isotonic sodium chloride solution. Furthermore, a well-defined volume, typically 2 ml of a liquid haemolysis agent H has been filled into the receptacle 32, typically having a capacity of 2 ml. (It should be noted here, that a dry haemolysis agent may be used as an alternative.) Finally, the receptacle 31, typically having a capacity of 3 ml, is filled with a washing liquid, typically isotonic sodium chloride solution. The receptacles 29 and 28, each typically having a capacity of 1 ml, are empty.

In the transport position, the capillary holder 46 is not completely introduced into the hole 41. The valve slide 54 is in a position where the mouths of the channels 35, 36, 37, 38 and 39 are covered by smooth, unrecessed portions of the valve slide surface 54a. Consequently, all these channels are closed in relation to the valve slide.

FIG. 4 shows the sampling position. The capillary holder has been pulled out of the hole 41, and a blood sample S is taken with the capillary tube as illustrated in FIG. 4. The tube is approached to a drop of blood B formed on a punctured finger tip F, and the drop is sucked up by capillary action to completely fill the capillary tube 46 with a defined volume of sample S, typically 10 µl. After the sample is taken, the capillary tube is re-inserted into the hole 41 and pushed into its fully inserted position shown in FIG. 7. In that position, the rear portion of the capillary holder body 48 having a non-shown O-ring effectively seals the body 48 in the hole 41. The valve slide is still in its original position.

FIG. 5 shows the first diluting or mixing step. The valve slide 54 is displaced such that one end of its cross-channel 55 communicates with the channel 37 and the other end thereof communicates with the channel 39. Since the annular groove 52 is located opposite to the hole 42 in the fully introduced position, communication is now established between the receptacle 28 and the receptacle 33.

Now, diluting agent $D_1$ is caused to flow from the receptacle 33 through the channel 39, the valve channel 55, and the channel 37 into the relatively narrow portion 41c of the hole 41. There, a part of the flow is directed through the capillary tube 47, thus displacing the blood sample S contained therein into the cross-channel 52 and the annular groove 51. Another part of the flow is directed along the exterior of the protruding end of the capillary tube into the slot 53 and from there into the cross-channel 52 and the annular groove 51 where it meets the blood sample and mixes therewith and dilutes it. Together the two flows will end up in the receptacle 28. The mixture is then caused to flow back along the same two paths into the receptacle 33, where it mixes with the remainder of the diluting agent $D_1$ still contained therein.

The flow back and forth is repeated until a proper mixing is ensured. When the first mixing step is completed, a defined volume of first step diluted sample $(S+D_1)$ remains within the valve slide channel 55. This is due to the typical volume relations between the receptacles 28 and 33, that ensures that the receptacle 33 will never be emptied. With the typical volumes stated, the dilution ratio after the first step is 1:200.

The second dilution and mixing step is shown in FIG. 6. The valve slide 54 is further displaced such that one end of its cross-channel 55 communicates with the channel 35 and the other end thereof communicates with the channel 36, thus establishing communication between the receptacles 29 and 30. In the displacement of the valve slide, the defined volume of first stage diluted sample previously entrapped in the slide channel 55 is brought along. Simultaneously, one end of the first leg 56a of the L-shaped channel 56 is brought into communication with the channel 37, one end of the second leg 56b is brought into communication with the channel 38, and the common other end of the legs 56a and 56b is brought into communication with the channel 39. Thus, there is established simultaneous communication between the receptacles 28, 32 and 33.

The second mixing step includes two parallel parts.

A first part takes place between receptacles 29 and 30. The diluting liquid $D_2$ in the receptacle 30 is caused to flow through the channel 36, into the slide channel 55 displacing the entrapped volume of first stage diluted sample, through the channel 35 and into the originally empty receptacle 29.

A second part takes place between the receptacles 28, 32 and 33, the receptacles 28 and 33 both containing the first step diluted sample $(S+D_1)$ and the receptacle 32 containing a haemolysis agent H. The liquids are caused to flow back and forth between the three receptacles until a proper mixing is ensured. In case the haemolysis agent is dry, it will be successively dissolved during the repeated flushing of the receptacle 32. The second part of the second mixing step is stopped with a main portion of the mixture $(S+D_1+H)$ remaining within the receptacle 33. This mixture has a dilution ratio of 1:400 with the typical volumes stated, and is for white blood cell testing.

The housing 21 is preferably made from a translucent synthetic resin. This enables the provision of a light path 64 through the housing. A portion of the receptacle 33 is formed with a recess 65 having an accurately defined length and parallel end walls 66, 67. The recess extends diagonally across a corner of the housing 21, and the walls 22 and 25 of the housing are formed with planar wall portions 68, 68', parallel to the respective end wall 66, 67. The light path further includes a light source 69, preferably a light diode, and a light sensor 70. The light path enables photometric determination of certain parameters of the liquid contained in the receptacle 33, such as, initially, a reference value of the diluting liquid and the opposed walls of the recess 65, and then certain values of the final mixture.

Figure 11:
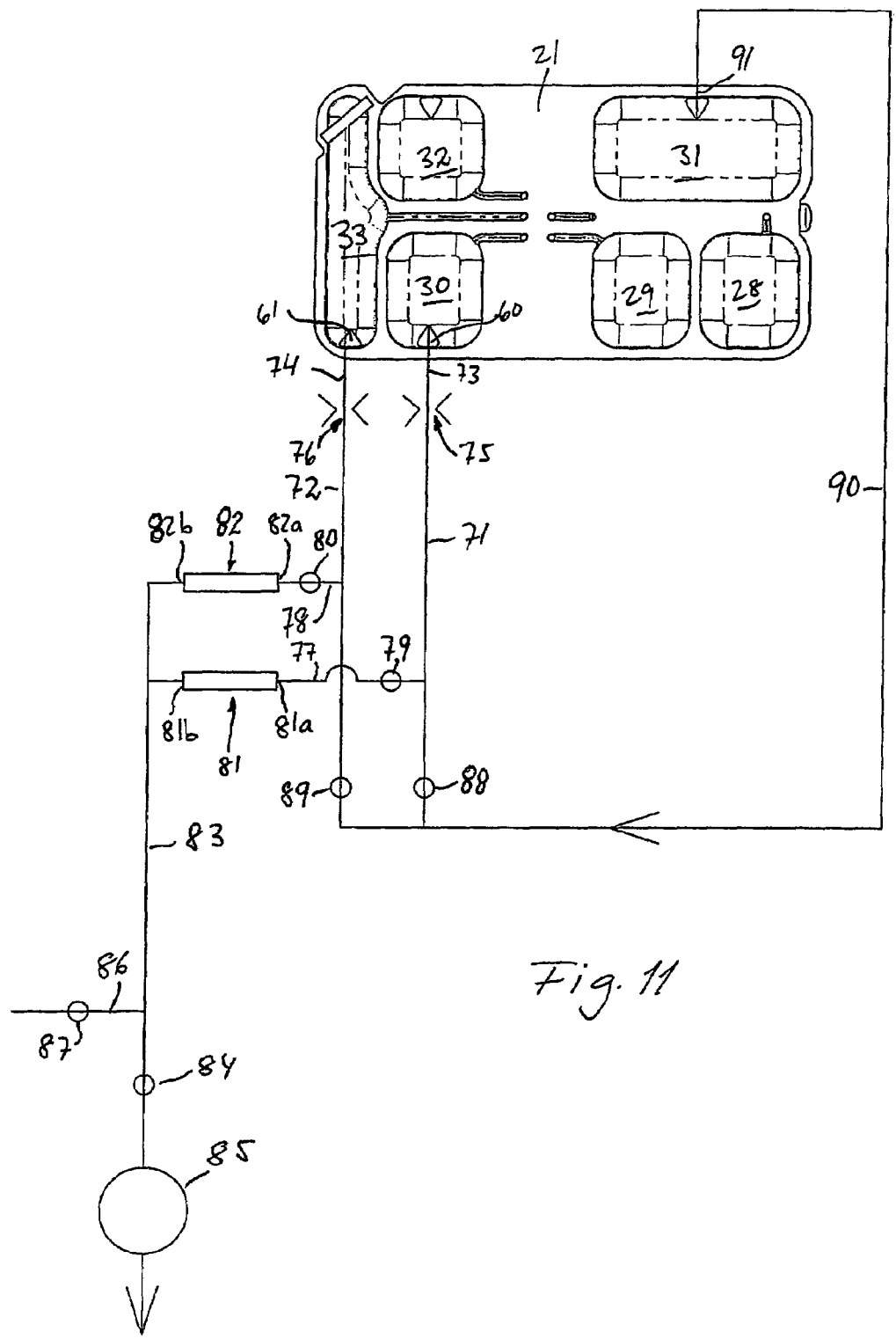
FIG. 11 is a schematic view showing the measuring step and the subsequent cleaning step.

Other tests to be performed on the diluted samples contained within the receptacles 30 and 33, involve withdrawal of fluid from the respective receptacles. This is performed by a measurement system schematically shown in FIG. 11. It includes two conduits 71, 72, each starting with a needle portion 73, 74, respectively. The needle portions are inserted through the respective plug sealing the openings 60, 61 into the receptacles 30, 33, respectively. Each of the conduits 71, 72 is provided with a cell counting station, each comprising an orifice 75, 76. As is known in the art, the orifices are small apertures allowing statistically only one blood cell to pass at a time. By means of non-shown electric wires, a voltage may be applied over the orifices, and any change in the resistance across the orifices, indicating the passage of a blood cell to be counted, may be detected by suitable electronic equipment included in the system, and the sum of all resistance changes detected corresponds to the number of blood cells having passed through the orifice.

Each of the conduits 71, 72 has a branch 77, 78, including a valve 79, 80, and a measuring portion 81, 82, respectively. The measuring portions are provided with counting start detectors 81a, 82a and counting stop detectors 81b, 82b spaced defined distances.

The branches 77, 78 are joined to a common conduit 83 having a valve 84 and a pump 85 therein. A branch 86 from the conduit 83 between the branches 77, 78 and the valve 84 has a valve 87 and is open to the atmosphere.

Beyond the respective branch 77, 78, the conduits 71, 72 have a valve 88, 89, respectively, and are joined to a common conduit 90 having in its end a needle portion 91 introduced through the non-shown plug 62 into the receptacle 31 containing washing liquid.

In the start position of measurement, the conduits 71, 72, and possibly also the conduit 90, are filled with a liquid, typically the same isotonic sodium chloride solution as that used in receptacles 30 and 31. The valves 88, 89 and 87 are closed, whereas the valves 79, 80 and 84 are opened. The pump 85 is started to withdraw liquid from the receptacles 30 and 33. When the liquid originally in the conduits 71 and 72 reach the respective counting start detector 81a, 82a, counting in the orifices 75, 76 is started. At that time, liquid from the respective receptacle 30, 33 has reached the orifices. Counting stops when the liquid has reached the respective counting stop detector 81b, 82b. At that time, liquid from the receptacles 30, 33 may not have reached into the branches 77, 78.

Subsequently, the valve 84 is closed and the valve 87 is opened, whereupon liquid is caused to return to the receptacles 30, 33, thereby returning the liquid within the measuring portions 81, 82 at least to the counting start detectors 81a, 82a. Then the valves 79, 80 and 87 are closed, and the valves 88 and 89 are opened to perform a cleaning step.

In the cleaning step, more liquid is caused to enter the receptacles 30 and 33, but is now withdrawn from the receptacle 31 at least until fresh liquid therefrom has reached both receptacles 30, 33. In this position, with all possibly contaminated objects and liquids safely kept within the cartridge, the needles 73, 74, 91 are withdrawn, and the cartridge is disposed of.

To perform displacement of liquids from and to the various receptacles, there are various methods available, from simply pressing a finger against a portion of the diaphragm 40 over a chosen receptacle, to applying a hydraulic or pneumatic pressure over selected portions of the diaphragm. According to the present invention it is preferred to apply a vacuum over portions of the diaphragm corresponding to a selected receptacle. To perform this operation, the cartridge is placed in an instrument indicated in FIGS. 5 and 6, including also the measurement system shown in FIG. 11. In FIG. 10, merely a portion of the instrument is shown. It includes a plurality of vacuum domes having outlines corresponding to those of selected receptacles. A vacuum dome 92 is shown to be located over the receptacle 28. It has a rim 93 sealing against the diaphragm 40 and a tubular stem portion 94 attachable to a non-shown source of vacuum. A vacuum applied in the dome 92 causes the diaphragm 40 to strive to adopt the upwardly convex shape illustrated at 40*a*, thus sucking liquid into the receptacle 28 from, e.g., the receptacle 33 in the position according to FIG. 5. A vacuum applied to the corresponding vacuum dome associated with the receptacle 33 causes the liquid to be withdrawn from the receptacle 28 and the diaphragm to assume the shape indicated at 40*b*. Evidently, the same shape would result from an overpressure within the vacuum dome.

Although a slide valve has been described herein, it is obvious that other kinds of valves may be used, such as primarily a turning valve.

Also, it is within the scope of the present invention to provide an apparatus having depressions defining receptacles and channels in more than one of its sides, e.g., in two opposite sides, and a valve between these sides.

The invention claimed is:

1. A disposable cartridge for use in blood testing comprising:
   (a) a housing including multiple depressions formed on one surface of said housing, each of said depressions defining a main portion of a receptacle and connecting to at least one of channels disposed within said housing;
   (b) a diaphragm sealing said multiple depressions and forming multiple said receptacle; portions of said diaphragm over said depressions being flexible; and
   (c) a slide valve disposed within said housing among said channels adapted to interconnect selected channels for directing flow between selected receptacles,
   wherein displacement of a valve slide of said slide valve interconnects selected channels between selected receptacles.

2. The disposable cartridge of claim 1, wherein one or more of said depressions includes a sealed opening adapted to interface with a needle of a cell counting device.

3. The disposable cartridge of claim 2, wherein at least one of said receptacles contains a liquid diluting agent.

4. The disposable cartridge of claim 3, wherein one of said receptacles contains a haemolysis agent.

5. The disposable cartridge of claim 1, wherein said slide valve comprises at least one channel in said valve slide in communication with a blood sampling capillary tube, and displacement of said valve slide causes displacing a volume of a blood sample within said channel of said valve slide into one of said receptacles.

6. The disposable cartridge of claim 1, wherein said housing has integrated therein a light path for performing photometric measurement on material contained in at least one of said receptacles.

7. The disposable cartridge of claim 1 further comprising an additional depression sealed by said diaphragm forming an additional receptacle; said additional depression having a sealed opening adapted to interface with a needle of a cell counting device; and said additional receptacle containing a washing liquid for cleaning said cell counting device.

8. The disposable cartridge of claim 1, wherein said valve slide comprises a valve channel having a defined volume disposed on a surface of said valve slide.

9. The disposable cartridge of claim 8, wherein said displacement of said valve slide interconnects selected receptacles through said valve channel.

10. The disposable cartridge of claim 9, wherein said displacement of said valve slide displaces a defined volume of a sample contained in said valve channel into one of said receptacles.

11. A disposable cartridge for use in blood testing comprising:
   (a) a housing including a generally flat top side and multiple depressions formed on said top side, each of said depressions defining a main portion of a receptacle and connecting to at least one of channels disposed within said housing;
   (b) a diaphragm sealingly attached to said top side of said housing, covering said multiple depressions and forming multiple said receptacle; portions of said diaphragm over said depressions being flexible; and
   (c) a slide valve comprising a valve slide having a valve channel disposed on a surface of said valve slide, said slide valve disposed within said housing among said channels adapted to interconnect selected channels for directing flow between selected receptacles through said valve channel; wherein displacement of said valve slide interconnects selected channels between selected receptacles through said valve channel.

12. The disposable cartridge of claim 11, wherein said displacement of said valve slide displaces a sample of said defined volume contained in said valve channel into one of said receptacles.

13. The disposable cartridge of claim 11, wherein at least one of said receptacles contains a liquid diluting agent.

14. The disposable cartridge of claim 11, wherein one of said receptacles contains a haemolysis agent.

15. The disposable cartridge of claim 11, wherein said housing has integrated therein a light path for performing photometric measurement on material contained in at least one of said receptacles.

16. The disposable cartridge of claim 11 further comprising an additional depression sealed by said diaphragm forming an additional receptacle; said additional depression having a sealed opening adapted to interface with a needle of a cell counting device; and said additional receptacle containing a washing liquid for cleaning said cell counting device.

17. A disposable cartridge for use in blood testing comprising:
   (a) a housing including a generally flat top side and multiple depressions formed on said top side, each of said depressions defining a main portion of a receptacle and connecting to at least one of channels disposed within said housing;
   (b) a diaphragm sealingly attached to said top side of said housing, covering said multiple depressions and forming multiple said receptacle; portions of said diaphragm over said depressions being flexible; and (c) a valve comprising at least one valve channel having a defined volume, said valve disposed within said housing among said channels adapted to interconnect selected channels between selected receptacles for directing flow between selected receptacles through said valve channel, wherein said valve displaces a sample with said defined volume entrapped in said at least one valve channel into selected channels between selected receptacles.

18. The disposable cartridge of claim 17, wherein at least one of said receptacles contains a liquid diluting agent.

19. The disposable cartridge of claim 17, wherein one of said receptacles contains a haemolysis agent.

20. The disposable cartridge of claim 17, wherein said housing has integrated therein a light path for performing photometric measurement on material contained in at least one of said receptacles.

21. The disposable cartridge of claim 17 further comprising an additional depression sealed by said diaphragm forming an additional receptacle; said additional depression having a scaled opening adapted to interface with a needle of a cell counting device; and said additional receptacle containing a washing liquid for cleaning said cell counting device.

* * * * *

UNITED STATES PATENT AND TRADEMARK OFFICE
CERTIFICATE OF CORRECTION

PATENT NO.       : 7,608,223 B2                                           Page 1 of 1
APPLICATION NO.  : 10/533790
DATED            : October 27, 2009
INVENTOR(S)      : Berndtsson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1183 days.

Signed and Sealed this

Twelfth Day of October, 2010

David J. Kappos
*Director of the United States Patent and Trademark Office*